United States Patent
Hu et al.

(10) Patent No.: US 10,633,315 B2
(45) Date of Patent: Apr. 28, 2020

(54) SYNTHESIS OF BICYCLO[2.2.2]OCTANES

(71) Applicant: Eastman Chemical Company, Kingsport, TN (US)

(72) Inventors: Yue Rachel Hu, Sunnyvale, CA (US); Robert Thomas Hembre, Johnson City, TN (US); Gerald Charles Tustin, Kingsport, TN (US); Christopher Harlan Burk, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/339,950

(22) PCT Filed: Oct. 11, 2017

(86) PCT No.: PCT/US2017/056027
§ 371 (c)(1),
(2) Date: Apr. 5, 2019

(87) PCT Pub. No.: WO2018/075301
PCT Pub. Date: Apr. 26, 2018

(65) Prior Publication Data
US 2020/0039906 A1 Feb. 6, 2020

Related U.S. Application Data

(60) Provisional application No. 62/409,928, filed on Oct. 19, 2016.

(51) Int. Cl.
*C07C 29/48* (2006.01)
*C07C 67/39* (2006.01)
*B01J 27/13* (2006.01)
*B01J 27/24* (2006.01)
*B01J 31/04* (2006.01)

(52) U.S. Cl.
CPC ............ *C07C 29/48* (2013.01); *B01J 27/13* (2013.01); *B01J 27/24* (2013.01); *B01J 31/04* (2013.01); *C07C 67/39* (2013.01); *B01J 2231/321* (2013.01); *B01J 2531/004* (2013.01); *C07C 2602/44* (2017.05)

(58) Field of Classification Search
CPC ..... C07C 29/48; C07C 67/39; C07C 2602/44; B01J 31/04; B01J 27/13; B01J 27/24; B01J 2531/004; B01J 2231/321
See application file for complete search history.

(56) References Cited

U.S. PATENT DOCUMENTS

| | | | |
|---|---|---|---|
| 3,081,334 A | 3/1963 | Kauer | |
| 3,228,984 A | 1/1966 | Humber | |
| 3,255,254 A | 6/1966 | Kauer | |
| 3,256,241 A | 6/1966 | Watson | |
| 3,301,827 A | 1/1967 | Martin | |
| 3,337,498 A | 8/1967 | Hogsed | |
| 3,367,941 A | 2/1968 | Gregory | |
| 3,533,594 A | 10/1970 | Segmüller | |
| 3,546,290 A | 12/1970 | Kauer | |
| 4,020,141 A | 4/1977 | Quinn | |
| 4,355,080 A | 10/1982 | Zannucci | |
| 4,448,998 A | 5/1984 | King | |
| 4,486,561 A | 12/1984 | Chung et al. | |
| 5,707,667 A | 1/1998 | Galt et al. | |
| 6,368,532 B1 | 4/2002 | Otoshi et al. | |
| 6,649,600 B1 | 11/2003 | Kiesman et al. | |
| 6,921,736 B1 | 7/2005 | Nolan | |
| 7,132,499 B2 | 11/2006 | Tobita et al. | |
| 7,781,562 B2 | 8/2010 | Crawford et al. | |
| 9,082,912 B2 | 7/2015 | Levy | |
| 9,328,050 B1 | 5/2016 | Boppana et al. | |
| 2006/0004151 A1 | 1/2006 | Shaikh et al. | |
| 2008/0053512 A1 | 3/2008 | Kawashima | |
| 2010/0324207 A1 | 12/2010 | Sturzel et al. | |
| 2014/0087990 A1* | 3/2014 | Kitamura | C11B 9/0053 512/22 |
| 2016/0039780 A1 | 2/2016 | Shi et al. | |

FOREIGN PATENT DOCUMENTS

| | | |
|---|---|---|
| FR | 1 374 693 | 10/1964 |
| GB | 1 024 487 | 3/1966 |
| JP | 06 032882 A | 2/1994 |
| WO | WO 00 47635 A1 | 8/2000 |

(Continued)

OTHER PUBLICATIONS

Geivandov, R. KH et al.; "New synthesis of 1,4-dihydroxybicyclo[2.2.2]octane" Zhurnal Organicheskoi Khimii; pp. 218-219; Jan. 1, 1979 (Original Language).
Adkins, Homer and Wojcik, Bruno; "Hydrogenation of Amides to Amines"; Journal of the American Chemical Society—Communications to the Editor; p. 247; 1934.
AGFA, Power by Technology; "UNIQOAT—The Single-Layer Backsheet"; 2 pages; Jun. 2018; retrieved from website: http://www.agfa.com/specialty_products/solutions/solar-pv-backsheet/uniqoat.
Bailey, William J. and Golden, Harold R.; "Cyclic Dienes. I. 1,2-Dimethylenecyclohexane"; Journal of the American Chemical Society; pp. 4780-4782; Oct. 5, 1953.
Baleizão, Carlos et al.; "Oxime Carbapalladacycle Covalently Anchored to High Surface Area Inorganic Supports or Polymers as Heterogeneous Green Catalysts for the Suzuke Reaction in Water"; Journal of Organic Chemistry, 69; pp. 439-446; 2004.

(Continued)

*Primary Examiner* — Rosalynd A Keys
(74) *Attorney, Agent, or Firm* — Tammye L. Taylor

(57) ABSTRACT

Provided is a process for the preparation of certain 1,4-bicyclo[2.2.2]octane derivatives. The new synthetic procedure involves treating 1,4-dimethylene cyclohexane with an oxidizing agent in the presence of a transition metal catalyst comprising a palladium compound to afford certain oxo-substituted bicyclo[2.2.2]octane species. The process of the invention thus affords a novel and simplified means for the commercial production of a wide variety of bicyclo[2.2.2]octane derivatives.

22 Claims, 2 Drawing Sheets

(56) References Cited

FOREIGN PATENT DOCUMENTS

| WO | WO 2006 128184 A2 | 11/2006 |
|---|---|---|
| WO | WO 2018 075301 A1 | 4/2018 |

OTHER PUBLICATIONS

Bedford, Robin B. et al.; "Silica-supported imine palladacycles-recyclable catalysts for the Suzuki reaction?"; Journal of Organometallic Chemistry, 633; pp. 173-181; 2001.
Carr, N. et al.; "A Comparison of the Properties of Some Liquid Crystal Materials Containing Benzene, Cyclohexane, and Bicyclo[2.2.2]octane Rings"; Molecular Crystals and Liquid Crystals, vol. 66; pp. 267-282; 1981.
Chang, Hexi, et al.; "Convenient One-Pot Preparation of Dimethyl Bicyclo[2.2.2]octane-1,4-dicarbolylate, a Key Intermediate for a Novel Adenosine $A_1$ Receptor Antagonist"; Synthetic Communications, vol. 37; pp. 1267-1272; 2007.
Clark, Jim; "Making Amines"; 6 pages; 2004, modified Mar. 2016; retrieved from website: https://www.chemguide.co.uk/organicprops/amines/preparation.html.
Corma, Avelino et al.; "A periodic mesoporous organosilica containing a carbapalladacycle complex as heterogeneous catalyst for Suzuki cross-coupling"; Journal of Catalysis, 229; pp. 322-331; 2005.
Corma, Avelino et al.; "An imidazolium ionic liquid having covalently attached an oxime carbapalladacycle complex as ionophilic heterogeneous catalysts for the Heck and Suzuki-Miyaura cross-coupling"; Tetrahedron, 60; pp. 8553-8560; 2004.
Dewar, Michael J. S. and Goldberg, Ronald S.; "The Role of p-Phenylene Groups in Nematic Liquid Crystals"; Journal of the American Chemical Society, 92:6; pp. 1582-1586; Mar. 25, 1970.
Dotrong, M. et al.; "Synthesis, Characterization, and Properties of Colorless Rigid-Rod Poly(benzobisthiazole) Derived from Bicyclo[2.2.2]octane"; Journal of Polymer Science: Part A: Polymer Chemistry, vol. 32; pp. 2953-2960; 1994.
Fehling; "Ueber die Bernsteinsäure und ihre Verbindungen"; Justus Liebigs Annalen der Chemie, 49; pp. 154-212; 1844 (Original Language).
Ferreira, Arthur Batista et al.; "Tin-Catalyzed Esterification and Transesterification Reactions: A Review"; International Scholarly Research Network (ISRN Renewable Energy), vol. 2012, Article ID 142857, 13 pages.
Friberg, Annika et al.; "Efficient bioreduction of bicyclo[2.2.2]octane-2,5-dione and bicyclo[2.2.2]oct-7-ene-2,5-dione by genetically engineered *Saccharomyces cerevisiae*"; Organic & Biomolecular Chemistry, 4; pp. 2304-2312; 2006.
Gu, Xin et al.; "Discovery of 4-heteroarylbicyclo[2.2.2]octyltriazoles as potent and selective inhibitors of 11β-HSD1: Novel therapeutic agents for the treatment of metabolic syndrome"; Bioorganic & Medicinal Chemistry Letters 15; pp. 5266-5269; 2005.
Guha, P. C.; "Para-Brückenbildung beim Succinylo-bernsteinsäure-äthylester, I. Mitteil.: Bildung von Bicyclo-[1.2.2]-heptan-, Bicyclo[2.2.2]octan- und Bicyclo-[3.2.2]-nonan-Systemen"; Chemische Berichte, vol. 72, Part 2; pp. 1359-1373; 1939 (Original Language).
Gürbüz, Nevin et al.; "Surface Modification of Inorganic Oxide Particles with a Carbene Complex of Palladium: A Recyclable Catalyst for the Suzuki Reaction"; Journal of Inorganic and Organometallic Polymers, vol. 14, No. 2; p. 149; Jun. 2004.
Guyer, von A. et al.; "197. Über die katalytische Reduktion aliphatischer Carbonsäureamide"; Helv. Chim. Acta, vol. XXXIII; pp. 1649-1654; 1955 (Original Language).
Harruna, Issifu I. and Polk, Malcolm B.; "Thermotropic Copolyesters. II. Synthesis and Characterization of Copolyesters Containing the Bicyclo[2.2.2]oct-2-ene Mesogenic Unit"; Journal of Polymer Science: Part A: Polymer Chemistry, vol. 26; pp. 2171-2182; 1988.
Harruna, Issifu I. and Polk, Malcolm B.; "Thermotropic Homopolyester. I. Synthesis and Characterization of Homopolyesters Containing the Mesogenic Unit, Bicyclo[2.2.2]oct-2-ene"; Journal of Polymer Science: Part A: Polymer Chemistry, vol. 28; pp. 285-298; 1990.
Harruna, Issifu I. and Polk, Malcolm B.; "Thermotropic copolyesters: 3. Synthesis and characterization of liquid crystal copolyesters containing the bicyclo[2.2.2]octane mesogenic unit"; Polymer Communications, vol. 32, No. 2; pp. 39-41; 1991.
He, De-Hua et al.; "Hydrogenation of Carboxylic Acids Using Bimetallic Catalysts Consisting of Group 8 to 10 and Group 6 or 7 Metals"; Tetrahedron Letters, vol. 36, No. 7; pp. 1059-1062; 1995.
Hirosawa, Chitaru et al.; "Hydrogenation of Amides by the Use of Bimetallic Catalysts Consisting of Group 8 to 10 and Group 6 or 7 Metals" Tetrahedron Letters, vol. 37, No. 37; pp. 6749-6752; 1996.
Holtz, Hans D. and Stock, Leon M.; "The Preparation of 1-Carobyx-4-substituted Bicyclo [2.2.2]octanes"; Journal of the American Chemical Society, vol. 86; pp. 5183-5188; Dec. 5, 1964.
Humber, L. G. et al.; "Agents Affecting Lipid Metabolism XIII. The Synthesis of 1,4-disubstituted Bicyclo[2.2.2]Octane Derivatives"; Candian Journal of Chemistry, vol. 42; pp. 2852-2861; 1964.
Kauer, J. C. et al; "Bridgehead-Substituted Bicyclo[2.2.2]octanes. I. Addition of Ethylene to Cyclohexa-1,3-diene-1,4-dicarboxylic Acid Derivatives"; Journal of Organic Chemistry, vol. 30; pp. 1431-1436; May 1965.
Kopecký, Jan and Šmejkal, Jaroslav; "Synthesis of Bridgehead Chloro- Bromo- and Iodobicyclo[2.2.2]octanes"; Collection Czechoslovak Chemical Communications, vol. 45; p. 2965; 1980.
Kopecký, Jan et al.; "Synthesis of Bridgehead Bicyclo[2.2.2]octanols"; Collection of Czechoslovak Chemical Communications, vol. 46; pp. 1370-1375; 1981.
Kopecký, Jan and Šmejkal, Jaroslav; "The Synthesis of 1,4-Dihydroxy- and 1,4-Dihalogenobicyclo[2.2.2]octanes"; Tetrahedron Letters, No. 40; pp. 3889-3891; Jul. 1967.
Kuehne, ME. E. and Lambert, B. F.; "1,4-Dihydrobenzoic Acid [2,5-Cyclohexadiene-1-carboxylic acid]"; Organic Synthesis, Coll., vol. 43; p. 22; 1963.
Lemouchi, Cyprien et al.; "Ultra-fast Rotors for Molecular Machines and Functional Materials via Halogen Bonding: Crystals of 1,4-Bis(iodoethynyl)bicyclo[2.2.2]octane with Distinct Gigahertz Rotation at Two Sites"; Journal of the American Chemical Society, vol. 133; pp. 6371-6379; 2011.
Lenz, Robert W. et al.; Properties of a liquid crystalline polyester with a mesogen containing the bicyclooctylene ring': Liquid Crystals, 4:3; pp. 317-323; 1989.
Liu, Yanchun; "Synthesis and Characterization of Amorphous Cycloaliphatic Copolyesters with Novel Structures and Architectures"; Liu Dissertation submitted to Virginia Polytechnic Institute and State University; 260 pages; Mar. 22, 2012.
Liu, Yanchun and Turner, Richard; "Synthesis and Properties of Cyclic Diester Based Aliphatic Copolyesters"; Journal of Polymer Science: Part A: Polymer Chemistry, vol. 48; pp. 2162-2169; 2010.
Magro, Angel A. Núñez et al.; "The synthesis of amines by the homogeneous hydrogenation of secondary and primary amides"; Chemical Communications; pp. 3154-3156; 2007.
Nuding, G. et al; "Rodlike Molecules by Kolbe Electrolysis"; Synthesis; pp. 71-76; Jan. 1996.
Otera, Junzo; "Transesterification"; Chemical Reviews, vol. 93; pp. 1449-1470; 1993.
Polk, Malcolm et al.; "Thermotropic Copolyesters Containing the Bicyclo[2.2.2]Octane Ring System"; Molecular Crystals and Liquid Crystals Incorporating Nonlinear Optics, vol. 157; pp. 1-11; 1988.
Polk, Malcolm and Onwumere, Fidelis C.; "Thermotropic Copolyesters. 1. Synthesis and Characterization of Liquid Crystal Copolyesters Containing the Bicyclo[2.2.2]octane Ring System"; Journal Macromolecular Science-Chem., A23 (3); pp. 423-432; 1986.
Polk, Malcolm B. et al.; "Thermotropic Copolyesters. II. Synthesis and Characterization of Liquid-Crystal Copolyesters Containing the Bicyclo[2.2.2]Octane Ring System"; Journal of Polymer Science: Park A: Polymer Chemistry, vol. 24; pp. 1923-1931; 1986.
Polk, Malcolm B. et al.; "Thermotropic Copolyesters. III. Synthesis and Characterization of Liquid Crystal Copolyesters Containing the Bicyclo[2.2.2]octane Ring System"; Journal of Polymer Science: Park A: Polymer Chemistry, vol. 26; pp. 2405-2422; 1988.
Polshettiwar, Vivek et al.; "Silica-supported palladium: Sustainable catalysts for cross-coupling reactions"; Coordination Chemistry Reviews, vol. 253; pp. 2599-2626; 2009.

(56) References Cited

OTHER PUBLICATIONS

Roberts, John D. et al.; "Syntheses of Some 4-Substituted Bicyclo[2.2.2]octain-1-carboxylic Acids"; Journal of the American Chemical Society, vol. 75; pp. 637-640; Feb. 5, 1953.
Scheiner, Peter et al.; "Snthesis of Bicyclic Nitriles and Related Compounds. II"; Journal of Organic Chemistry, vol. 28; pp. 2960-2965; 1963.
Taimr, Ludek and Smith, James G.; "Polyesters Containing Bicyclo[2.2.2]octane and Bicyclo[3.2.2]nonane Rings"; Journal of Polymer Science: Part A-1, vol. 9; pp. 1203-1211; 1971.
Weis, Robert et al.; "4-Aminobicyclo[2.2.2]octanone Derivatives with Antiprotozoal Activities"; Monatshefte für Chemie (Chemical Monthly), vol. 134; pp. 1019-1026; 2003.
Whitney, Joel G. et al.; "Antiviral Agents. I. Bicyclo[2.2.2]octan- and -oct-2-enamines"; Journal Medical Chemistry, vol. 13; pp. 254-260; Mar. 1970.
Zhdankin, Viktor V.; "Hypervalent iodine(III) reagents in organic synthesis" APKIVOC—Special Issue Reviews and Accounts, (i); pp. 1-62; 2009.
Notification of Transmittal of the International Search Report and the Written Opinion of the International Searching Authority, or the Declaration dated Dec. 19, 2017 received in International Application No. PCT/US2017/056027.
Notification of Transmittal of the International Search Report and the Written Opinion of the International Searching Authority, or the Declaration dated Jan. 4, 2019 received in International Application No. PCT/US2018/055138.
Co-pending U.S. Appl. No. 16/219,085, filed Dec. 13, 2018; David Scott Porter.

* cited by examiner

SYNTHESIS OF BICYCLO[2.2.2]OCTANES

CROSS-REFERENCE TO RELATED APPLICATION(S)

This application is a national stage filing under 35 USC § 371 of International Application Number PCT/US2017/056027, filed on Oct. 11, 2017, which claims the benefit of the filing date to U.S. Provisional Application No. 62/409,928, filed on Oct. 19, 2016, the entire disclosures of which are incorporated by reference herein.

FIELD OF THE INVENTION

This invention relates to the field of organic synthesis. In particular, it relates to a process for preparing a variety of 1,4-(substituted) bicyclo[2.2.2]octane derivatives.

BACKGROUND OF THE INVENTION

Bicyclo[2.2.2]octanes substituted at 1- and/or 4-positions are of great commercial interest. See, for example: (a) Joel G. Whitney, W. A. Gregory, J. C. Kauer, J. R. Roland, Jack A. Snyder, R. E. Benson and E. C. Hermann "Antiviral agents. I. Bicyclo[2.2.2]octan- and -oct-2-enamines" J. Med. Chem., 1970, 13, 254-60; (b) U.S. Pat. No. 3,546,290. (c) "4-Pyridyl and 4-(substituted-pyridyl) bicyclo[2.2.2]octane-1-amines" U.S. Pat. No. 3,367,941; and (d) Bicyclo [2.2.2] Acid GPR120 Modulators, US Pat. Appl. 2016/0039780.

Unfortunately, the bridgehead substituents of various bicyclic systems inclusive of the bicyclo[2.2.2]octane system are inert to nucleophilic substitution. Therefore, it would be useful to develop simple methods of preparation of the bridgehead bicyclo[2.2.2]octane derivatives. 1,4-Diacetoxybicyclo[2.2.2]octane is particularly interesting because it is a potential starting material for the preparation of various bridgehead bicyclo[2.2.2]octane derivatives. By way of example, U.S. Pat. No. 6,649,600 teaches various adenosine receptor antagonists, such compounds containing bridgehead bicyclo[2.2.2]octane substituents, which can be prepared from 1,4-diacetoxybicyclo[2.2.2]octane.

Bicyclo[2.2.2]octane derivatives also serve as important intermediates in the synthesis of natural products such as terpenes and alkaloids. (see, for example, Org. Biomol. Chem., 2006, 4, 2304-2312). They are also important building blocks for therapeutic agents for the treatment of metabolic syndrome (see, for example, Bioorg. Med. Chem. Lett., 2005, 15, 5266-5269) and other diseases (Org. Biomol. Chem., 2006, 4, 2304-2312).

Moreover, bicyclo[2.2.2]octane diols and diacids are useful as specialty monomers for certain polymers. See, for example, (a) G.B. 1,024,487; (b) J. Polym. Sci. Part A, 2010, Vol. 48, pp. 2162-2169; (c) U.S. Pat. No. 3,256,241; (d) U.S. Pat. No. 3,081,334; (e) Mol. Cryst. Liq. Cryst., 1981, Vol. 66, pp. 267-282; (f) J. Polym. Sci. A, 1994, Vol 32, pp. 2953-2960; and (g) J. Am. Chem. Soc. 1970, Vol 92, pp. 1582-1586.

Existing methods for the production of bicyclo[2.2.2] octane 1,4-substituted derivatives often involve expensive and toxic reagents, salt-forming reactions, costly reaction conditions, and suffer from poor net yields. (See, for example, Kopecký, Jan; Jaroslav, Šmejkal; and Vladimír, Hanuš; Synthesis of bridgehead bicyclo[2.2.2]octanols, Coll. Czech. Chem. Commun. 1981, 46, 1370-1375.) The reaction sequence is given in Scheme 1 below. Acid-catalyzed reaction of isopropenyl acetate with 1,4-cyclohexanedione provides (besides 1,4-diacetoxy-1,4-cyclohexadiene) 1,4-diacetoxy-O-cyclohexadiene (1) which undergoes diene cycloaddition with maleic anhydride to provide 1,4-diacetoxybicyclo[2.2.2]oct-5-ene-2,3-dicarboxylic acid anhydride (II). Hydrogenation of (II) provides the saturated III which was hydrolyzed to the corresponding dicarboxylic acid (IV). Oxidative decarboxylation of (IV) with lead tetraacetate in pyridine in the presence of oxygen gave 1,4-diacetoxybicyclo[2.2.2]oct-2-ene (V) which upon hydrogenation gave diacetate (VI). The overall yield was reported to be 28-31%.

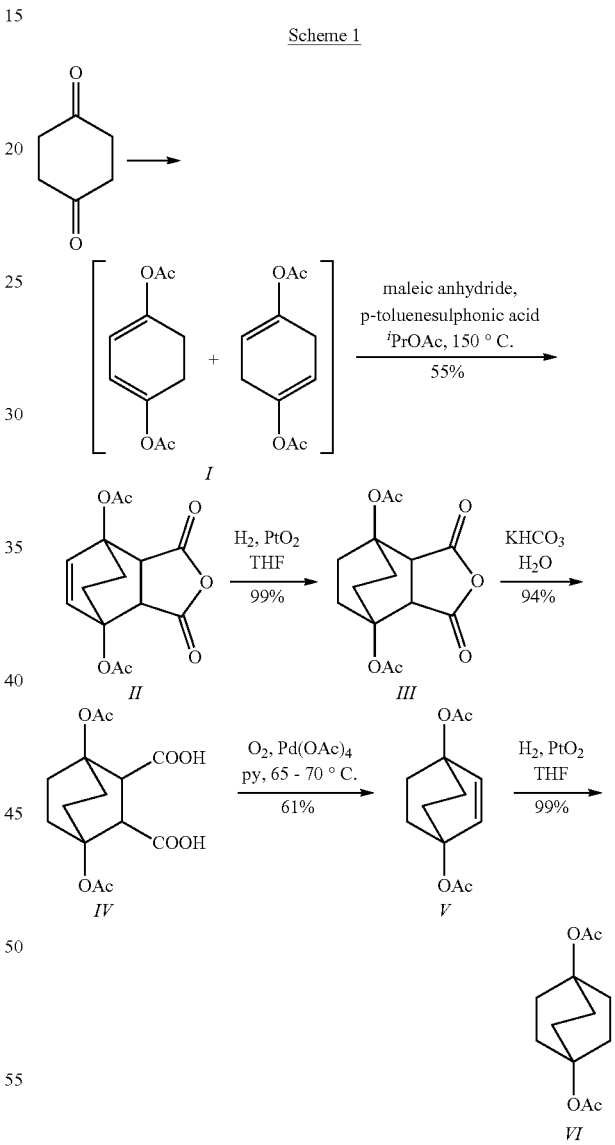

Scheme 1

Ac = CH₃CO

Beginning with 1,4-CHDM (1,4-cyclohexane dimethanol), a two-step conversion to 1,4-dimethylene cyclohexane is known (Scheme 2). (See J. Am. Chem. Soc., 1953, 75, 4780-4782.)

Scheme 2

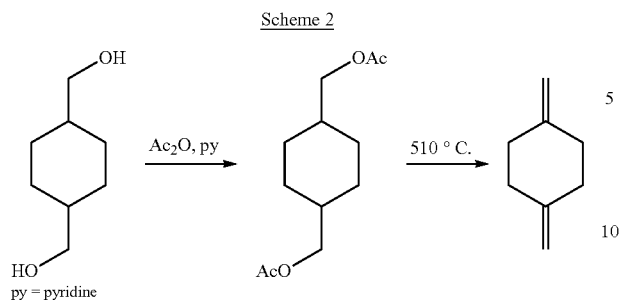

py = pyridine

SUMMARY OF THE INVENTION

The invention is as set forth in the appended claims. Briefly, in one embodiment, the invention provides a process for preparing compounds of Formula (I):

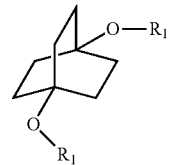
(I)

wherein each $R_1$ is independently hydrogen or a group of the formula

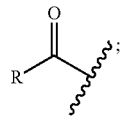

which comprises contacting a compound of the formula

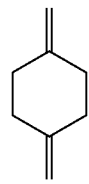

with (i) a transition metal catalyst comprising a palladium compound and (ii) an oxidizing agent;
optionally in the presence of at least one of
(I) compound of the formula

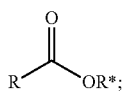

wherein R is chosen from hydrogen; and $C_1$-$C_{12}$ alkyl, optionally substituted by one or more of groups chosen from $C_1$-$C_6$ alkoxy, halo, nitro, and cyano; R* is chosen from hydrogen; $C_1$-$C_{12}$ alkyl, optionally substituted by one or more of groups chosen from $C_1$-$C_6$ alkoxy, halo, nitro, and cyano; and an alkali metal cation; or
(II) a compound having at least one $C_1$-$C_{12}$ alkanoyloxy moiety of the formula

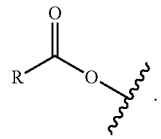

In certain embodiments, the process of the invention generally provides a mixture of compounds represented by the various substituents defined above by R, when a carboxylic acid of the formula RC(O)OH is present and/or a compound or solvent with such an alkanoyloxy (or carboxylate) group is present. In the processes of the invention, varying proportions of the mixture of compounds of formula (A), (B), and (C) can be produced; generally, the relative proportions are dependent upon reaction conditions, the choice of oxidizing agent, and whether a carboxylic acid or other alkanoyloxy moiety-containing compound (i.e., carboxylate) source (such as ethyl acetate as solvent) is present.

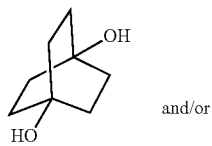
(A)
and/or

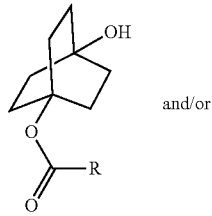
(B)
and/or

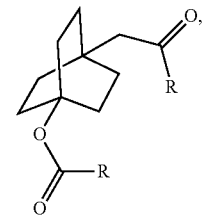
(C)

wherein R is as defined herein.
When such a carboxylic acid and/or a compound or solvent with such an alkanoyloxy moiety (or carboxylate) is not present, the process provides exclusively a product of the formula

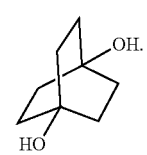
(A)

The process of the invention thus represents a novel transition metal-catalyzed chemical transformation. The method features the high conversion yield of 1,4-dimethylene cyclohexane to various 1,4-(substituted)bicyclo[2.2.2]octanes. The process of the invention thus affords a novel and simplified means for the commercial production compounds of formulae (A), (B), and (C), which can in turn be separated and/or subjected to further synthetic organic transformations to provide a wide variety of useful compounds having bridgehead (i.e., 1, 4-) bicyclo[2.2.2]octane substituents.

DETAILED DESCRIPTION OF THE INVENTION

Figure 1:
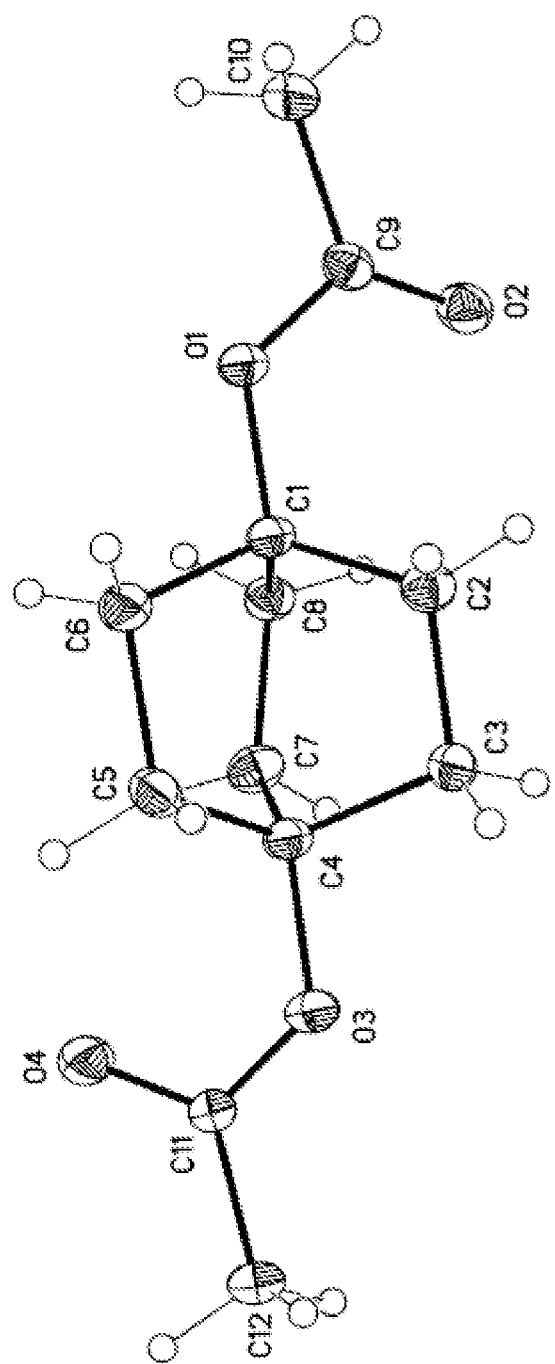
FIG. 1 depicts the molecular structure of 1,4-diacetoxy-bicyclo[2.2.2]octane prepared via Example 1 below. Selected bond distances (Å) and angles (deg): O(1)-C(1) 1.4623(11), C(1)-C(2) 1.5273(14), C(2)-C(3) 1.507(7), C(3)-C(4) 1.587(6), C(4)-O(3) 1.4671(12), O(1)-C(1)-C(2) 112.68(8), C(1)-C(2)-C(3) 110.0(3), C(2)-C(3)-C(4) 108.1(4), C(3)-C(4)-O(3) 105.1(3), C(3)-C(4)-C(5) 105.3(3), C(2)-C(1)-C(8) 110.16(8).

In a first embodiment, the invention provides a process for preparing compounds of Formula (I):

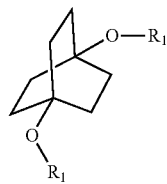

(I)

wherein each $R_1$ is independently hydrogen or a group of the formula

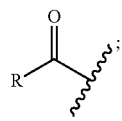

which comprises contacting a compound of the formula

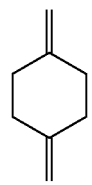

with (i) a transition metal catalyst comprising a palladium compound and (ii) an oxidizing agent;
optionally in the presence of at least one of
(I) compound of the formula

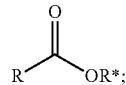

wherein R is chosen from hydrogen; and $C_1$-$C_{12}$ alkyl, optionally substituted by one or more of groups chosen from $C_1$-$C_6$ alkoxy, halo, nitro, and cyano; R* is chosen from hydrogen; $C_1$-$C_{12}$ alkyl, optionally substituted by one or more of groups chosen from $C_1$-$C_6$ alkoxy, halo, nitro, and cyano; and an alkali metal cation; or
(II) a compound having at least one $C_1$-$C_{12}$ alkanoyloxy moiety of the formula

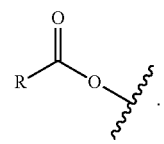

In another embodiment, the invention provides a process for preparing a compound of the formula:

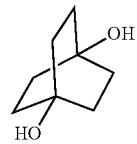

(A)

which comprises contacting a compound of the formula

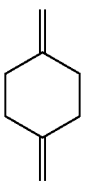

with (i) a transition metal catalyst comprising a palladium compound, and (ii) an oxidizing agent, in the absence of
(I) a compound of the formula

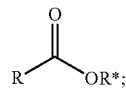

wherein R is chosen from hydrogen; and $C_1$-$C_{12}$ alkyl, optionally substituted by one or more of groups chosen from $C_1$-$C_6$ alkoxy, halo, nitro, and cyano; R* is chosen from hydrogen; $C_1$-$C_{12}$ alkyl, optionally substituted by one or more of groups chosen from $C_1$-$C_6$ alkoxy, halo, nitro, and cyano; and an alkali metal cation; and
(II) a compound having at least one $C_1$-$C_{12}$ alkanoyloxy moiety of the formula

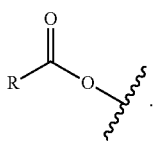

In a further embodiment, the invention provides a process for preparing compounds of the formulae:

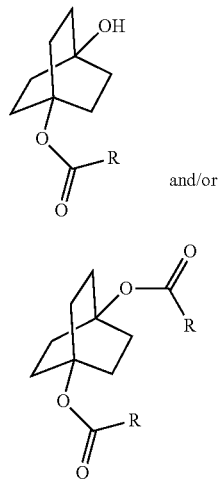

which comprises contacting a compound of the formula

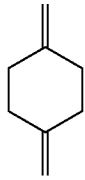

with a carboxylic acid of the formula

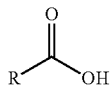

wherein each R is independently hydrogen, or a $C_1$-$C_{12}$ alkyl group, in the presence of (i) a transition metal catalyst comprising a palladium compound, and (ii) an oxidizing agent.

As noted above, varying proportions of the mixture of compounds of formula (A), (B), and (C) can be produced; generally, the relative proportions are dependent upon reaction conditions, the choice of oxidizing agent, and whether a carboxylic acid or other alkanoyloxy moiety-containing compound (i.e., carboxylate) source (such as ethyl acetate as solvent) is present.

Additionally, under certain conditions, the formation of (A) appears to require water in addition to an oxidizing agent such as hydrogen peroxide when a carboxylic acid of the formula RC(O)OH is present. In this regard, when iodosobenzene diacetate was used as oxidant in the presence of water, no products of the formulae (A), (B) and (C) were observed. Otherwise, a compound of formula (A) can be prepared as the sole bicyclooctane product by the process of the invention when said process is conducted in the absence of compounds containing an alkanoyloxy moiety as set forth above.

In another embodiment, when air was used as oxidant in the presence of ethylacetate, products of the formulae (A) and (B) were predominantly observed with the diol (A) formed as minor product, perhaps due to the presence of water (in the air or in the ethyl acetate). Accordingly, in another embodiment, compounds (A), (B) and (C) are prepared by treating 1,4-dimethylene cyclohexane with hydrogen peroxide, palladium diacetate and acetic acid. The hydrogen peroxide used can be commercially available 30% solution in water or some other concentration of $H_2O_2$ in water. In another embodiment of the invention, compounds (B) and (C) are prepared by treating 1,4-dimethylene cyclohexane with iodosobenzene diacetate, palladium diacetate, acetic acid, and dimethylsulfoxide (DMSO). In another embodiment of the invention, (B) and (C) are prepared by bubbling air through a mixture of 1,4-dimethylene cyclohexane, palladium diacetate and acetic acid.

In the experiments below, the compounds of formulae (A), (B) and (C) were produced/co-produced in varying proportions. If desired, they may be separated post-reaction using known separation techniques such as precipitation, recrystallization, extraction, vacuum distillation or liquid chromatography. As can be seen from Example 3, the use of palladium diacetate, acetic acid, and 30% $H_2O_2$ in water provided the 1,4-diol product (A), in addition to compounds (B) and (C). In another experiment (Example 6), it can be seen that the 1,4-diol product can be the exclusive product if no carboxylic acid or other alkanoyloxy source, such as "acetate" from ethyl acetate solvent is present.

In one embodiment of this process the carboxylic acid is a liquid under the reaction condition and is capable of dissolving all reaction components. Examples of carboxylic acids which are believed to be suitable include formic acid, acetic acid ("AcOH"), propionic acid, butyric acid, isobutyric acid, tert-butyric acid, valeric acid, caproic acid, enanthic acid, caprylic acid, capric acid, hendecanoic acid, and lauric acid, and the like. In the case of any such acid which is a solid at room temperature, a suitable solvent is utilized as discussed below. In another embodiment an in situ generated carboxylic acid is also believed to be suitable. (See Example 8 below, which is believed to generate acetic acid in situ as the acetone is oxidized by hydrogen peroxide to acetic acid.) In this regard, we note that control experiments utilizing $PdCl_2$/acetone/$MnO_2$, bis(dibenzylideneacetone)palladium(0), palladium metal, and palladium diacetate/iodosobenzene/dimethylsulfoxide do not provide products of the formulae (A), (B), or (C) above. In one embodiment, the carboxylic acid is acetic acid. The amount of carboxylic acid used with respect to the 1,4-dimethylene cyclohexane starting material is not particularly limited, and can be chosen in accordance with the amount of 1,4-dimethylene cyclohexane, the composition of the catalyst, or the reaction conditions. In one embodiment, the carboxylic acid is utilized in a range of about 0 to 20 molar equivalents relative to the diene. The carboxylic acid can also be replaced or partly replaced by or other alkanoyloxy-containing sources, such as "acetate" from ethyl acetate solvent. In Example 1 below, the reaction resulted in compounds of formulae (B) and (C) in a roughly 2:1 ratio.

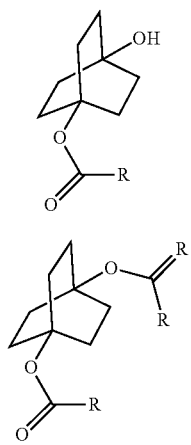

As noted above, a transition metal catalyst comprising a palladium compound is utilized in the process of the invention. In one embodiment, the catalyst is palladium diacetate. In other embodiments (see EXAMPLES 10-12), suitable catalysts include palladium chloride, ammonium hexachloropalladate(IV), and palladium trifluoroacetate. Bis(dibenzylideneacetone)palladium(0) was found to be unsuitable. Examples of other palladium compounds we believe suitable to catalyze the desired reaction include bis(propionyloxy)palladium, bis(butyryloxy)palladium, sodium palladium tetraacetate, sodium palladium tetrachloride, (1,2-bis(phenylsulfinyl)ethane)palladium diacetate, palladium nitrate, palladium sulfate, palladium bromide, and palladium iodide. These palladium compounds may be used individually or in combination. The amount of palladium compound used with respect to the 1,4-dimethylene cyclohexane starting material is not particularly limited, and can be chosen in accordance with the molar ratio of carboxylic acid with respect to 1,4-dimethylene cyclohexane, the composition of the catalyst, and reaction conditions, etc. In one embodiment, the ratio of catalyst to diene is about 0.01% to 20%, and in another embodiment, is about 0.1% to 5%. In other embodiments, the ratio of catalyst to diene is about 1%, about 3%, or about 5%. In general terms, if too little catalyst is used, the reaction tends to progress too slowly and results in undesired side reactions; if too much catalyst is used, the reaction becomes expensive and also results in undesired side reactions.

The palladium compound can also be immobilized on a support to facilitate catalyst recycling. The palladium compound(s) can be physisorbed on a support, or alternately, may be anchored on a support via a chemical bond to prevent leaching. Both inorganic materials and organic materials can be used as catalyst supports. Examples of inorganic supports include carbon, silica ($SiO_2$), $Al_2O_3$, $MgCl_2$, MgO, $ZrO_2$, $TiO_2$, $B_2O_3$, CaO, ZnO, $CaF_2$, $MgF_2$, zeolite or $SiO_2$-$Al_2O_3$, and $SiO_2$—MgO, and a mixture of each of these inorganic materials or silica mixed with small amounts of other inorganic materials.

Examples of conventional organic support include polystyrene, polyethylene, polyurea, cyclohextrine, cellulose, etc, which can maintain solid shapes in the reaction mixture and thus can be easily removed by physical means, e.g. filtration. When using an inorganic support, the metal compound is chemically bonded to a functional group on the support surface. The functional group can be pre-attached to the support. In the case of an organic support, the functional group can be introduced by a copolymerization with a monomer containing a functional group. Alternately, the functional group can be attached to an organic support, which is then chemically reacted with a ligand on a pre-catalyst to yield a supported catalyst. Supported catalysts via chemical bonding can be prepared by known methods. See, for example "Silica-supported palladium: Sustainable catalysts for cross-coupling reactions" Coord. Chem. Rev. 2009, 253 2599-2626; WO 00/47635; and U.S. Pat. No. 6,921,736, incorporated herein by reference.

In one embodiment, a ligand is anchored on a support via a chemical bond and then the palladium compound is ligated. A ligand generally contains functional groups that have one or more atoms having free electrons to coordinate/donate to the metal. Examples of functional groups include thiol, thiourea, amine, diamine, triamine, cysteine, imidazole, etc. More examples can be found in "Silica-supported palladium: Sustainable catalysts for cross-coupling reactions" Coord. Chem. Rev. 2009, 253 2599-2626.

In a further embodiment, a pre-catalyst complex with a functional group on a ligand is synthesized which is then anchored on a support by a reaction between the functional group on a ligand and that on a support surface. See, for example, 1) J. Organomet. Chem. 2001, 633 173-181; 2) J. Catal. 2005, 229 322-331; 3) Tetrahedron 2004, 60 8553-8560; 4) J. Org. Chem. 2004, 69 439-446; and 5) J. Inorg. Organomet. Polym. 2004, 14 149.

In a further embodiment, the transition metal catalyst comprising a palladium compound can be immobilized to a support using encapsulation technology. For example, by using microencapsulation technology, a compound comprising palladium, such as palladium acetate can be immobilized within a highly cross-linked polyurea matrix.

The transition metal catalyst comprising a palladium compound and the support can also be added separately to a reaction mixture to effect the immobilization in-situ. The supported single-site catalyst can facilitate catalyst recycling via simple filtration or other physical/mechanical processes. The metal compound dissolved in reaction solution can be efficiently removed by treatment with metal scavengers.

In one embodiment, the term "alkali metal cation" refers to $Li^+$, $K^+$, $Cs^+$, and Nat The oxidizing agent or "oxidant" is generally a co-reactant and is chosen to oxidize the palladium compound to a higher oxidation state (i.e., wherein at least a portion of the palladium species is >2); for example, Pd(II) can be oxidized to the +3 or +4 oxidation state in order to prevent precipitation of the catalyst and to keep the metal at the effective oxidation state in order to properly catalyze the desired reaction. Attempts with benzoquinone, iodosobenzene ditrifluoroacetate, and meta-chloroperoxybenzoic acid (mCPBA) have not been successful under the experimental conditions of Example 1 below.

In one embodiment, the oxidizing agent is iodosobenzene diacetate. Other iodosoarene dicarboxylates with the following structure are also believed to be suitable:

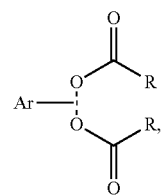

wherein Ar denotes an aryl group such as phenyl or naphthyl, optionally substituted by one or more substituents selected from $C_1$-$C_6$ alkyl, $C_1$-$C_6$ alkoxy, $C_1$-$C_6$ alkoxycarbonyl, $C_1$-$C_6$ alkanoyl oxy, $C_1$-$C_6$ alkanoylamino, halogen, carboxy, cyano, nitro, $C_1$-$C_6$ alkylsulfonyl, hydroxyl, $C_1$-$C_6$ alkylene-OH, $C_1$-$C_6$ alkylene-$CO_2$H, and the like, and wherein R is as defined above. In another embodiment, the oxidizing agent is iodosobenzene dipivalate. The in-situ generated iodosoarene dicarboxylates are also believed to be suitable. Other iodonium salts or 1(111) (Iodine (III)) oxidants are also believed to be suitable. In another embodiment, the oxidizing agent is a peroxide such as hydrogen peroxide or peracetic acid as well as other organic or inorganic peroxides, including peroxides generated in situ. In general, organic and inorganic peroxides are also believed to be suitable; mCPBA was tested but resulted in no reaction under the reaction conditions of the experimental section below. In another embodiment, the oxidizing agent is manganese dioxide. In another embodiment, solid oxidant Oxone®, potassium peroxymonosulfate available from ALFA, is utilized as the oxidant in the process. Other solid oxidants that are strong enough to oxidize palladium compound to a desired oxidation state are also believed to be suitable. In another embodiment, the oxidizing agent is air. Oxygen (or ozone), (either in pure form or mixed with other gases, e.g., nitrogen, argon and $N_2O$) are believed to be suitable. Other oxidants that are believed to be suitable include $Ag_2CO_3$, $K_2S_2O_8$, $HNO_3$, AgOAc, $Cu(OAc)_2$, $Mn(OAc)_3$ and Wacker oxidation systems. The amount of oxidizing agent used with respect to the 1,4-dimethylene cyclohexane is not particularly limited, but is in one embodiment one or more molar equivalents to that of the 1,4-dimethylene cyclohexane. In another embodiment, the range is about one to five equivalents. In the case of $H_2O_2$ as oxidizing agent, if less than one equivalent is used, the reaction fails to go to full conversion.

The presence of a cosolvent is not generally required, except for those situations where the carboxylic acid is a solid at the reaction temperature. If a co-solvent is utilized, the ratio of cosolvent to carboxylic acid is not particularly limited and is set in accordance with the mole ratio of carboxylic acid with respect to 1,4-dimethylene cyclohexane, the composition of the catalyst, or the reaction conditions. In one embodiment, a solvent that can coordinate with the metal center (for example, a nitrogen-containing solvent) can be utilized. In another embodiment, the solvent if utilized is dimethyl sulfoxide. The cosolvent may be replaced by external ligands. Further solvents which are believed to be suitable include acetonitrile, benzonitrile, dimethylformamide, dimethylacetamide, dimethyl sulfone, 1,2-bis(phenylsulfinyl)ethane and its derivatives, nitrogenous ligands such as pyridine and pyridine derivatives, imidazole and imidazole derivatives, 4,5-diazafluorenone, bipyridine, phenanthroline, bipyrimidine, bipyridine, phenanthroline derivatives, and N-alkyl pyrrolidones such as N-methyl pyrrolidone and N-n-butyl pyrrolidone. Other common organic solvents that can dissolve reactants and are compatible to the current experimental condition are also believed to be suitable. The solvent should be compatible with the oxidizing agent. The choice of solvent depends on the reaction conditions and the oxidizing agent. Examples of solvents include but are not limited to polar aprotic solvents such as ethyl acetate and other alkyl acetates, acetonitrile, acetone, or THF; and non-polar solvents such as heptane, toluene, and xylene.

Reaction conditions such as reaction temperature and reaction time are not particularly limited, and they may be set in accordance with the mole ratio of carboxylic acid with respect to 1,4-dimethylene cyclohexane, or the composition of the catalyst. In certain embodiments utilizing palladium diacetate as the transition metal catalyst comprising palladium, the range of temperature is 10° C. to 60° C. and the range of reaction time is generally 3 hours to 60 hours. For other catalysts, reaction conditions may vary. The reaction can be run as a batch or continuous process.

The novel transformation presented in the present invention is not readily predictable. For instance, when the cyclic structure of dimethylene cyclohexane is absent and two olefins are separated by two methylene groups, as in 1,5-hexadiene, the Pd-catalyzed diacetoxylation favors formation of a five-membered rather than a six-membered ring (eq 2).

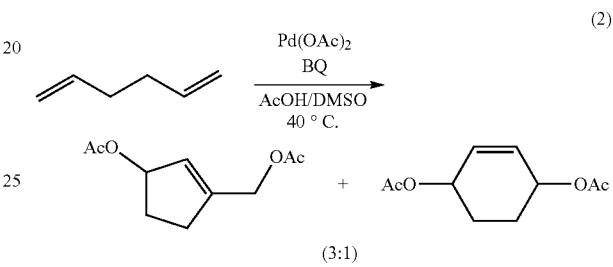

(2)

Under the conditions of Example 1, the reaction of dimethylene cyclohexane is essentially quantitative to a single product core structure represented by formulae (B) and (C).

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein. As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as nonpatent literature, is hereby incorporated by reference in their entirety. To the extent that any incorporated subject matter contradicts with any disclosure herein, the disclosure herein shall take precedence over the incorporated content.

This invention can be further illustrated by the following examples of certain embodiments thereof, although it will be understood that these examples are included merely for purposes of illustration and are not intended to limit the scope of the invention unless otherwise specifically indicated.

EXAMPLES

Preparation of 1,4-dimethylene cyclohexane 1,4-Dimethylene cyclohexane was prepared by following the literature procedure with small modifications. (J. Am. Chem. Soc., 1953, 75, 4780-4782). 1,4-Cyclohexanedimethanol (CHDM) (3,250 g, 22.5 mol) and pyridine (5.5 g, 0.07 mol) were heated to 125° C. in a 20-liter reactor fitted with dropping funnel and reflux condenser. Over a period of 2 hours, acetic anhydride (7020 g, 68.8 mol) was added to the glycol. After the addition, the mixture was stirred for 1.5 hours at 125° C. After acetic acid and anhydride were removed by vacuum distillation, CHDM diacetate (5,100 g, 99% yield) was collected. The reaction was also successfully performed using DMAP and Nafion as catalyst.

At a rate of 0.5 g per minute, 2,000 g (8.8 mol) of CHDM diacetate was dropped into a 1-in. quatz column heated to 540° C. by a Lindberg/Blue M furnace (Model number: HTF55347C) and paced to a depth of 27 in. with 0.25-in. quatz chips. The addition was conducted in nitrogen atmosphere by introducing a slow stream of nitrogen (25 ccm) at the top of the column. The pyrolysate was collected in a 3-liter flask cooled in an ice bath. GC-MS of the pyrolysate shows mainly 1,4-dimethylene cyclohexane and acetic acid with trace amount of unreacted CHDM diacetate and (4-methylenecyclohexyl)methyl acetate. Distillation of the pyrolysate gives azeotrope that contains 1, 4-dimethylene cyclohexane and acetic acid with a mole ratio of 1:2. Pure 1,4-dimethylene cyclohexane can be obtained by washing the azeotrope with distilled water.

Example 1

1,4-Dimethylene cyclohexane (1 g, 9.3 mmol), iodosobenzene diacetate (3.3 g, 10.2 mmol), palladium diacetate (100 mg, 0.45 mmol), acetic acid (10 mL), and DMSO (10 mL) were charged to a 100 mL round bottom flask equipped with a ¾ inch magnetic stir bar. The resulting mixture was purged with nitrogen to remove dissolving air. The suspension was stirred at room temperature until all white solids disappeared. Besides acetic acid and DMSO, the GC-MS spectrum of the reaction mixture at this point showed only iodobenzene, 1,4-diacetoxybicyclo[2.2.2]octane (its structure is further confirmed by $^1$H NMR and X-ray crystallography), and 4-acetoxybicyclo[2.2.2]octan-1-ol, indicating stoichiometric conversion of dimethylene cyclohexane. The ratio of 1,4-diacetoxybicyclo[2.2.2]octane to 4-acetoxybicyclo[2.2.2]octan-1-ol is 1:2 based on $^1$H NMR.

The orange reaction mixture was then quenched with saturated sodium bicarbonate ($NaHCO_3$) aqueous solution, extracted with 20 mL×3 diethyl ether. The combined diethyl ether layer was sequentially washed with 10 mL saturated $NaHCO_3$ aqueous solution, 10 mL distilled water, and 10 mL brine, and dried over $MgSO_4$. After filtration, 150 mL n-pentane was added to the diethyl ether solution and the resulting mixture was filtered through a short silica flash column and concentrated under reduced pressure (GC-MS showed there are iodobenzene, 1,4-diacetoxybicyclo[2.2.2] octane and 4-acetoxybicyclo[2.2.2]octan-1-ol in the concentrated mixture). Pure 1,4-diacetoxybicyclo[2.2.2]octane was isolated as a white crystalline solid by prep TLC. It's $^1$H NMR spectra in $CDCl_3$ features two singlets at δ 2.04 ppm and 1.87 ppm with the integration ratio of 2:1, consistent with the literature report. (see Jan Kopecký, et al.)

The crystals of 1,4-diacetoxybicyclo[2.2.2]octane suitable for X-ray crystallography were obtained by slowly evaporating the diethyl ether solvent from its concentrated diethyl ether solution. The crystal structure of 1,4-diacetoxybicyclo[2.2.2]octane is shown in FIG. 1.

The structure in FIG. 1 was solved and refined using the Bruker SHELXTL Software Package, using the space group Pbca, with Z=8 for the formula unit, C12H18O4. The final anisotropic full-matrix least-squares refinement on $F^2$ with 186 variables converged at R1=2.99%, for the observed data and wR2=8.18% for all data. The goodness-of-fit was 1.139. The largest peak in the final difference electron density synthesis was 0.214 $e^-/Å^3$ and the largest hole was −0.165 $e^-/Å^3$ with an RMS deviation of 0.030 $e^-/Å^3$. On the basis of the final model, the calculated density was 1.276 $g/cm^3$ and F(000), 976 $e^-$.

Compound 4-acetoxybicyclo[2.2.2]octan-1-ol is a pale yellow liquid. A singlet at δ 1.91 ppm on its $^1$H NMR spectra in $CDCl_3$ corresponds to the acetate methyl group. The structure of 4-acetoxybicyclo[2.2.2]octan-1-ol is not confirmed by other analytical methods. But a mixture of 1,4-diacetoxybicyclo[2.2.2]octane and 4-acetoxybicyclo[2.2.2] octan-1-ol were converted to a single diol, bicyclo[2.2.2] octane-1,4-diol, after alcoholysis with n-butanol or methanol (see Example 2).

Example 2

The concentrated reaction mixture from Example 1 (It contains 1,4-diacetoxybicyclo[2.2.2]octane, 4-acetoxybicyclo[2.2.2]octan-1-ol and iodobenzene.) was mixed with 10 mL n-butanol or methanol and one drop of sufuric acid in a 100 mL round bottom flask. The mixture was stirred at 80° C. for 3 h (with n-butanol) or 60° C. for 6 h (with methanol). After the reaction mixture was cooled to room temperature, all liquids were removed under vacuum. Diethyl ether (10 mL) was added to the brown sticky residue and the resulting off-white precipitates were collected through filtration, washed with 5 mL×3 diethyl ether, and dried in air (1.12 g, 85.5%). GC-MS analysis shows there is only one compound, namely bicyclo[2.2.2]octane-1,4-diol, in the precipitates. Its $^1$H NMR spectra in DMSO-$d_6$ features a sharp singlet at δ 1.58 ppm and a broad singlet at δ 3.93 ppm, consistent with the literature report. (Coll. Czech. Chem. Commun. 1981, 46, 1370-1375). The crystals of bicyclo [2.2.2]octane-1,4-diol suitable for X-ray crystallography were obtained by slowly evaporating the methanol from the corresponding alcoholysis mixture. The crystal structure of bicyclo[2.2.2]octane-1,4-diol is shown in FIG. 2.

Figure 2:
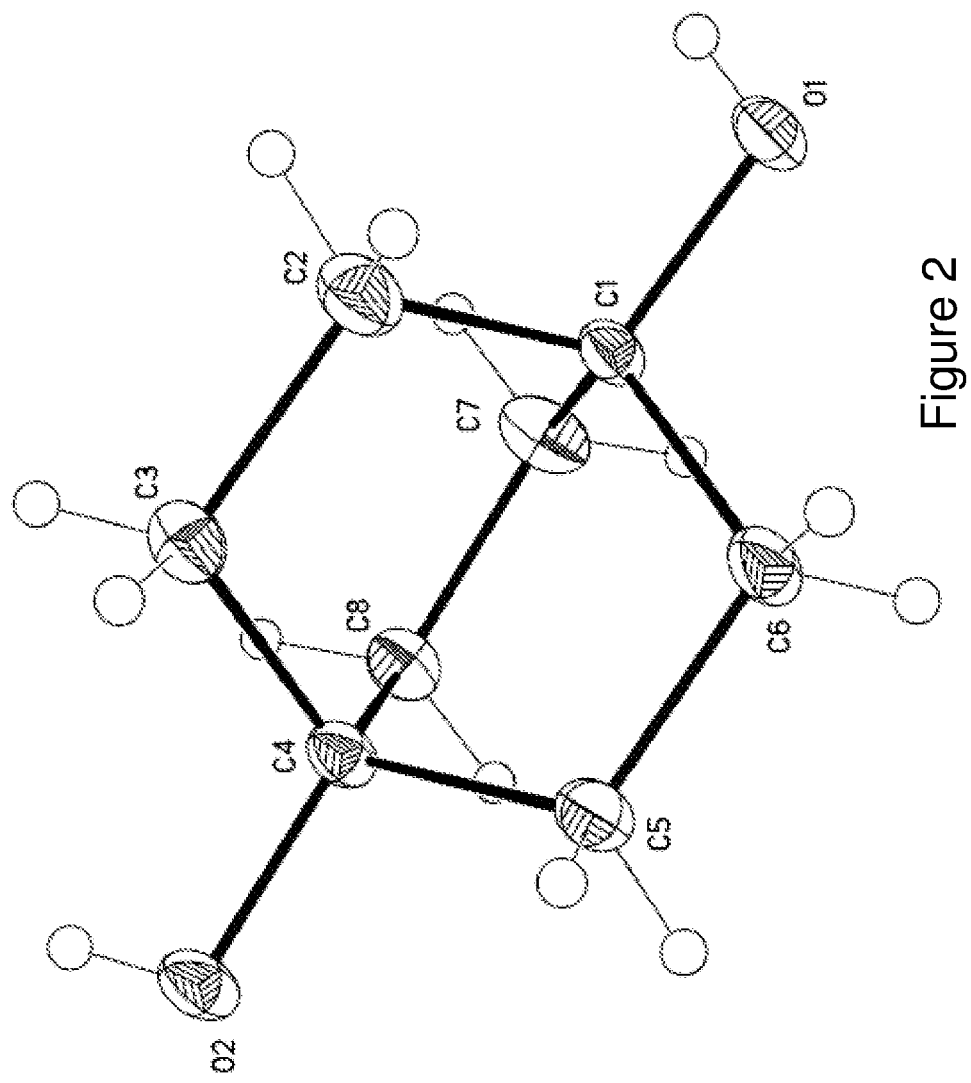
FIG. 2 depicts the molecular structure of bicyclo[2.2.2]octane-1,4-diol prepared via Example 2 below. Selected bond distances (Å) and angles (deg): O(1)-C(1) 1.4321(18), C(1)-C(2) 1.528(3), C(2)-C(3) 1.541(2), C(3)-C(4) 1.530(2), C(4)-O(2) 1.4339(18), O(1)-C(1)-C(2) 110.96(15), C(1)-C(2)-C(3) 109.65(15), C(2)-C(3)-C(4) 109.52(14), C(3)-C(4)-O(2) 110.70(14), C(3)-C(4)-C(8) 108.85(15), C(2)-C(1)-C(7) 108.63(15).

The structure in FIG. 2 was solved and refined using the Bruker SHELXTL Software Package, using the space group I41cd, with Z=16 for the formula unit, $C_{81}H_{14}O_2$. The final anisotropic full-matrix least-squares refinement on $F^2$ with 99 variables converged at R1=3.51%, for the observed data and wR2=9.81% for all data. The goodness-of-fit was 1.066. The largest peak in the final difference electron density synthesis was 0.259 $e^-/Å^3$ and the largest hole was −0.163 $e^-/Å^3$ with an RMS deviation of 0.037 $e^-/Å^3$. On the basis of the final model, the calculated density was 1.153 $g/cm^3$ and F(000), 1248 $e^-$.

The above reaction can also be catalyzed by other transesterification catalysts, including but not limited to inorganic acids (e.g. sulfuric acid, hydrogen chloride), inorganic bases (e.g. sodium hydroxide, potassium hydroxide), transition metal complexes (e.g. Sn, Ti), and other solid acids and bases.

Example 3

1,4-Dimethylene cyclohexane (1 g, 9.3 mmol), palladium diacetate (100 mg, 0.45 mmol), and acetic acid (5 g), were charged to a 100 mL round bottom flask equipped with a ¾ inch magnetic stir bar. To the resulting mixture, which was cooled with ice bath, 30% of hydrogen peroxide aqueous solution (1.5 g) was added dropwise under rapid stirring. The resulting yellow solution was stirred at room temperature for 6 hours and analyzed by GC-MS and GC, showing 4-acetoxybicyclo[2.2.2]octan-1-ol as the major product together with bicyclo[2.2.2]octane-1,4-diol and 1,4-diacetoxybicyclo[2.2.2]octane. The conversion of 1,4-Dimethylene cyclohexane was 59.7%. The selectivities of 4-acetoxybicyclo[2.2.2]octan-1-ol, 1,4-diacetoxybicyclo[2.2.2]octane and bicyclo[2.2.2]octane-1,4-diol were 52.6%, 22.4%, 19.3%.

After 6 hours, further conversion was observed when fresh 1,4-dimethylene cyclohexane and hydrogen peroxide were added to the above reaction mixture, indicating the catalytic system was still reactive.

Example 4

Palladium diacetate (224 mg, 1 mmol), 3-aminopropyl-functionalized silica gel (~1 mmol/g $NH_2$, 2 g), and acetone (50 g) were charged to a 100 mL round bottom flask equipped with a ¾ inch magnetic stir bar. The resulting suspension was stirred at 50 Celsius until the solution became colorless. The immobilized $Pd(OAc)_2/SiO_2$ catalyst was collected via filtration, washed with acetone and dried at 60 Celsius for overnight.

1,4-Dimethylene cyclohexane (100 mg, 0.93 mmol), the above immobilized $Pd(OAc)_2/SiO_2$ (100 mg), 30% hydrogen peroxide (200 mg) and acetic acid (1 g), were charged to a 5-mL glass vial equipped with a ⅜ inch magnetic stir bar. The resulting mixture was stirred at room temperature for 6 hours. After filtration, the solution was analyzed by GC. The solid catalyst was washed with acetone three times, dried in the oven, and reused under the above condition. The results summarized in Table 1 indicate the immoblized $Pd(OAc)_2/SiO_2$ catalyst is active and recyclable.

TABLE 1

Conversion and selectivity with recyclable $Pd(OAc)_2/SiO_2$ catalyst

| Catalyst | Conversion (%) | 4-acetoxybicyclo[2.2.2]octan-1-ol (%) | 1,4-diacetoxybicyclo[2.2.2]octane (%) | bicyclo[2.2.2]octane-1,4-diol (%) |
|---|---|---|---|---|
| Fresh $Pd(OAc)_2/SiO_2$ | 43.1 | 60.6 | 8.4 | 23.5 |
| Recycled $Pd(OAc)_2/SiO_2$ | 34.6 | 66.3 | 7.7 | 26.0 |

Example 5

1,4-Dimethylene cyclohexane in acetic acid (20 g, 0.084 mol, based on NMR purity, remainder acetic acid), palladium diacetate (0.567 g, 0.0025 mol, 3 mol %), and ethyl-acetate (25 mL) were charged to a 125 mL flask. To the flask was added 30% $H_2O_2$ (21.42 g, 0.189 mol, 2.25 eq) dropwise over ca. 3 hours keeping the reaction below 35° C. The reaction was stirred overnight. To the reaction mixture was added a 35% sodium metabisulfite solution (35.9 g in 66.7 g water) dropwise. The reaction was slightly exothermic. The two-phase mixture was filtered and separated. The aqueous phase was extracted with ethyl acetate (3×, 50 mL). The organic extracts were combined, dried over $MgSO_4$ and concentrated in vacuo to afford a pale yellow oil (14.8 g). Analysis by GCMS showed the oil to be a mixture of 4-acetoxybicyclo[2.2.2]-octan-1-ol (major product) and bicyclo[2.2.2]octane-1,4-diol.

Example 6

1,4-Dimethylene cyclohexane (5 g, 0.046 mol) and palladium dichloride (0.248 g, 0.0014 mol, 3 mol %) were added to a 125 mL flask. To the flask was added 25% oxone aqueous solution (28.27 g, 0.092 mol, 2 eq) dropwise over ca. 2 hours. The reaction was exothermic. The reaction mixture was stirred overnight. Analysis by GCMS showed conversion to bicyclo[2.2.2]octane-1,4-diol. The reaction mixture was filtered to remove undissolved $PdCl_2$. The aqueous solution was extracted 4× with n-butanol. The organic extracts were combined, dried over $MgSO_4$ and concentrated in vacuo to afford a dark residue. Analysis by GCMS confirmed that bicyclo[2.2.2]octane-1,4-diol was present with trace n-butanol.

Example 7

1,4-Dimethylene cyclohexane (50 mg, 0.46 mmol), palladium diacetate (5 mg, 0.02 mmol), manganese dioxide (50 mg), and acetic acid (1 g) were charged to a 5-mL glass vial equipped with a ⅜ inch magnetic stir bar. The resulting mixture was stirred at room temperature for overnight. After filtration, the solution was analyzed by GC-MS, which shows the presence of 1,4-diacetoxybicyclo[2.2.2]octane as the major product, trace amount of 4-acetoxybicyclo[2.2.2]octan-1-ol and a couple of unidentified byproducts.

Example 8

1,4-Dimethylene cyclohexane (50 mg, 0.46 mmol), palladium diacetate (5 mg, 0.02 mmol), 30% hydrogen peroxide (0.1 g), and acetone (1 g) were charged to a 5-mL glass vial equipped with a ⅜ inch magnetic stir bar. The resulting mixture was stirred in open air at room temperature for overnight and analyzed by GC-MS, which shows clean conversion of 1,4-dimethylene cyclohexane (67.4% conversion) to 4-acetoxybicyclo[2.2.2]octan-1-ol (44.5%) and bicyclo[2.2.2]octane-1,4-diol (55.5%).

Example 9

1,4-Dimethylene cyclohexane (50 mg, 0.46 mmol), palladium chloride (3.5 mg, 0.02 mmol), 30% hydrogen peroxide (0.1 g), and acetic acid (1 g) were charged to a 5-mL glass vial equipped with a ⅜ inch magnetic stir bar. The resulting mixture was stirred at room temperature for overnight and analyzed by GC-MS, which shows presence of 4-acetoxybicyclo[2.2.2]octan-1-ol, 1,4-diacetoxybicyclo[2.2.2]octane and bicyclo[2.2.2]octane-1,4-diol.

Example 10

1,4-Dimethylene cyclohexane (50 mg, 0.46 mmol), ammonium hexachloropalladate(IV) (5 mg), 30% hydrogen peroxide (0.1 g), and acetic acid (1 g) were charged to a 5-mL glass vial equipped with a ⅜ inch magnetic stir bar. The resulting mixture was stirred at room temperature for overnight and analyzed by GC-MS, which shows presence of 4-acetoxybicyclo[2.2.2]octan-1-ol, 1,4-diacetoxybicyclo[2.2.2]octane and bicyclo[2.2.2]octane-1,4-diol.

Example 11

1,4-Dimethylene cyclohexane (50 mg, 0.46 mmol), palladium trifluoroacetate (5 mg), 30% hydrogen peroxide (0.1 g), and acetic acid (1 g) were charged to a 5-mL glass vial equipped with a ⅜ inch magnetic stir bar. The resulting mixture was stirred at room temperature for overnight and analyzed by GC-MS, which shows presence of 4-acetoxybicyclo[2.2.2]octan-1-ol, 1,4-diacetoxybicyclo[2.2.2]octane and bicyclo[2.2.2]octane-1,4-diol.

Example 12

1,4-Dimethylene cyclohexane (5 g, 0.046 mol), ethylacetate (ca. 20 mL) and palladium diacetate (0.310 g, 0.0014 mol, 3 mol %) were added to a 125 mL flask. The reaction was stirred for 20 hours at room temperature as air was bubbled through the mixture. Analysis by GC-MS showed 4-acetoxybicyclo[2.2.2]octan-1-ol and bicyclo[2.2.2]octane-1,4-diol, but the major product was high molecular weight unknowns. No product isolation was attempted.

Example 13

1,4-Dimethylene cyclohexane (5 g, 0.046 mol), acetic acid (ca. 20 mL) and palladium diacetate (0.310 g, 0.0014 mol, 3 mol %) were added to a 125 mL flask. The reaction was stirred for 20 hours at room temperature as air was bubbled through the mixture. Analysis by GC-MS showed 4-acetoxybicyclo[2.2.2]octan-1-ol and 1,4-diacetoxybicyclo[2.2.2]octane, but the major product was high molecular weight unknowns. No product isolation was attempted.

Example 14

1,4-Dimethylene cyclohexane (5 g, 0.046 mol) and palladium diacetate (0.310 g, 0.0014 mol, 3 mol %) were added to a 125 mL flask. To the flask was added 32% peracetic acid (21.85 g, 0.092 mol, 2 eq) dropwise over ca. 3 hours. The reaction was stirred vigorously and evolved bubbles with a slight exotherm. The reaction was stirred for 18 hours. Analysis by GCMS showed 4-acetoxybicyclo[2.2.2]octan-1-ol as the major product with bicyclo[2.2.2]octane-1,4-diol present as well. No isolation was attempted.

Example 15

In a 25 mL round bottom flask, 2 g of the product mixture from EXAMPLE 5 was mixed with 10 mL acetic anhydride and 0.5 mL pyridine. The resulting mixture was stirred at 100 Celsius for 4 hours and cooled to room temperature. The solution after filtration was analyzed by GC-MS. Both 4-acetoxybicyclo[2.2.2]octan-1-ol and bicyclo[2.2.2]octane-1,4-diol were converted cleanly to 1,4-diacetoxybicyclo[2.2.2]octane.

Comparative Example 1,5-Hexadiene (1 g, 12.2 mmol), benzoquinone (2.6 g, 24.4 mmol), palladium diacetate (100 mg, 0.45 mmol), AcOH (10 mL), and DMSO (10 mL) were charged to a 100 mL round bottom flask equipped with a ⅓ inch magnetic stir bar. The resulting mixture was purged with nitrogen to remove dissolving air. The suspension was stirred at 40° C. for overnight (~12 h). A pale yellow liquid (640 mg) was obtained after the same workup as shown in Example 1, containing (3-acetoxycyclopent-1-en-1-myl) ethyl acetate and cyclohex-2-ene-1,4-diyldiacetate in a 3:1 ratio as confirmed by $^1$H NMR, $^{13}$C NMR, HSQC and GC-MS (molecular weight). The attempt of separating (3-acetoxycyclopent-1-en-1-yl)methyl acetate and cyclohex-2-ene-1,4-diyl diacetate by flash chromatography was not successful.

We claim:

1. A process for preparing compounds of Formula (I):

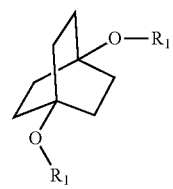

wherein each $R_1$ is independently hydrogen or a group of the formula

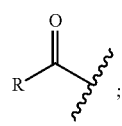

which comprises contacting a compound of the formula

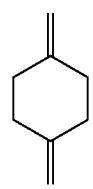

with (i) a transition metal catalyst comprising a palladium compound and (ii) an oxidizing agent;

optionally in the presence of at least one of
(I) a compound of the formula

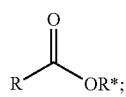

wherein R is chosen from hydrogen; and $C_1$-$C_{12}$ alkyl, optionally substituted by one or more of groups chosen from $C_1$-$C_6$ alkoxy, halo, nitro, and cyano;
R* is chosen from hydrogen; $C_1$-$C_{12}$ alkyl, optionally substituted by one or more of groups chosen from $C_1$-$C_6$ alkoxy, halo, nitro, and cyano; and an alkali metal cation; or
(II) a compound having at least one $C_1$-$C_{12}$ alkanoyloxy moiety of the formula

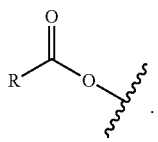

2. A process for preparing a compound of the formula:

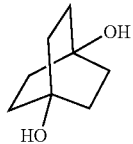
(A)

which comprises contacting a compound of the formula

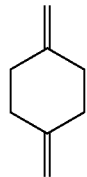

with (i) a transition metal catalyst comprising a palladium compound, and (ii) an oxidizing agent, in the absence of a
(I) compound of the formula

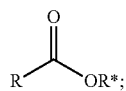

wherein R is chosen from hydrogen; and $C_1$-$C_{12}$ alkyl, optionally substituted by one or more of groups chosen from $C_1$-$C_6$ alkoxy, halo, nitro, and cyano;
R* is chosen from hydrogen; $C_1$-$C_{12}$ alkyl, optionally substituted by one or more of groups chosen from $C_1$-$C_6$ alkoxy, halo, nitro, and cyano; and an alkali metal cation; and
(II) a compound having at least one $C_1$-$C_{12}$ alkanoyloxy moiety of the formula

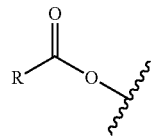

3. The process of claim 1 or 2, wherein R* is hydrogen.
4. The process of claim 1 or 2, wherein R is methyl.
5. The process of any one of claim 1 or 2, wherein the palladium compound is selected from palladium acetate, bis(propionyloxy)palladium, bis(butyryloxy)palladium, sodium palladium tetraacetate, sodium palladium tetrachloride, palladium trifluoroacetate, (1,2-bis(phenylsulfinyl)ethane)palladium diacetate, ammonium hexachloropalladate (IV), palladium nitrate, palladium sulfate, palladium chloride, palladium bromide, and palladium iodide.
6. The process of any one of claim 1 or 2, wherein the palladium compound selected from palladium acetate, palladium chloride, ammonium hexachloropalladate(IV), sodium palladium tetrachloride, and palladium trifluoroacetate.
7. The process of any one of claim 1 or 2, wherein the palladium compound is palladium chloride.
8. The process of any one of claim 1 or 2, wherein the palladium compound is palladium acetate.
9. The process of claim any one of claim 1 or 2, wherein the palladium compound is immoblized on an organic or inorganic support.
10. The process of any one of claim 1 or 2, wherein the oxidizing agent is chosen from organic and inorganic peroxides.
11. The process of any one of claim 1 or 2, wherein the oxidizing agent is hydrogen peroxide.
12. The process of any one of claim 1 or 2, wherein the oxidizing agent is peracetic acid.
13. The process of any one of claim 1 or 2, wherein the oxidizing agent selected from oxygen and oxygen-containing gases.
14. The process of any one of claim 1 or 2, wherein the oxidizing agent is oxygen or air.
15. The process of any one of claim 1 or 2, wherein the oxidizing agent comprises a solid oxidant.
16. The process of any one of claim 1 or 2, wherein the oxidizing agent comprises magnanese dioxide or potassium peroxy monosulfate.
17. The process of any one of claim 1 or 2, wherein the oxidizing agent comprises iodonium salts or Iodine(III) oxidizing agents.
18. The process of any one of claim 1 or 2, wherein the oxidizing agent is chosen from isolated or in-situ generated iodosoarene dicarboxylates.
19. The process of any one of claim 1 or 2, wherein the oxidizing agent is iodosobenzene diacetate.
20. The process of claim 1, further comprising the steps of hydrolysis and isolation of a compound of formula (A)

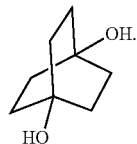
(A)

21. The process of claim 1, further comprising the step of isolating a compound of formula (B)
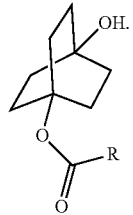
(B)
22. The process of claim 1, further comprising the step of isolating a compound of formula (C)
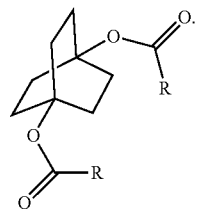
(C)
* * * * *